United States Patent [19]

Nazari

[11] Patent Number: 4,819,664
[45] Date of Patent: Apr. 11, 1989

[54] DEVICE FOR SELECTIVE BRONCHIAL INTUBATION AND SEPARATE LUNG VENTILATION, PARTICULARLY DURING ANESTHESIA, INTENSIVE THERAPY AND REANIMATION

[76] Inventor: Stefano Nazari, Via Bignanico, 12, Como, Italy

[21] Appl. No.: 159,426

[22] Filed: Feb. 17, 1988

Related U.S. Application Data

[63] Continuation of Ser. No. 890,199, Jul. 8, 1986, abandoned.

[30] Foreign Application Priority Data

Nov. 15, 1984 [IT] Italy ................. 23603 A/84
Jun. 5, 1985 [IT] Italy ................. 21025 A/85

[51] Int. Cl.[4] .............. A61M 16/00; A61M 29/00; A61M 15/00
[52] U.S. Cl. .................. 128/207.15; 604/96; 604/284
[58] Field of Search ............. 128/207.14, 207.15, 128/200.26, 326, 657, 341, 343, 345; 604/96, 104–109, 167, 166, 280, 283, 284

[56] References Cited

U.S. PATENT DOCUMENTS

| 3,799,173 | 3/1974 | Kamen | 128/207.15 |
| 4,248,221 | 2/1981 | Winnard | 128/207.15 |
| 4,344,436 | 8/1982 | Kubota | 604/284 |
| 4,351,328 | 9/1982 | Bodai | 128/207.15 |
| 4,453,545 | 6/1984 | Inove | 128/207.15 |
| 4,502,482 | 3/1985 | DeLuccia et al. | 128/207.15 |
| 4,607,635 | 8/1986 | Heydon | 128/207.15 |

FOREIGN PATENT DOCUMENTS

| 0064701 | 11/1982 | European Pat. Off. | 128/207.15 |
| 1505607 | 12/1967 | France | 128/207.15 |
| 541332 | 10/1973 | Switzerland | 128/207.15 |
| 124593 | 3/1959 | U.S.S.R. | 128/207.14 |
| 199338 | 9/1967 | U.S.S.R. | 128/207.15 |
| 908371 | 2/1982 | U.S.S.R. | 128/207.15 |
| 1528279 | 10/1978 | United Kingdom | 128/207.15 |

Primary Examiner—Edward M. Coven
Assistant Examiner—K. M. Reichle
Attorney, Agent, or Firm—Guido Modiano; Albert Josif

[57] ABSTRACT

The device comprises: a tracheal tube insertable into the trachea of a patient, and an endobronchial tube, of greater length than the tracheal tube and being insertable into the tracheal tube for reaching, with one of its extremities, one of the principal bronchi. In this way the endobronchial tube defines in co-operation with the tracheal tube a single air passage. At their external ends, the cited tubes are connectable to an air supply and at their internal ends are provided with sealing members which can be actuated to form a seal with the internal walls of the organs wherein the tubes are inserted. There are also provided stoppers adapted to act between the two tubes, towards the exterior, to prevent external communication with the cited air passage. The cited air passage and the endobronchial tube have substantially equal fluid-dynamic resistances to obtain uniform ventilation of both lungs.

3 Claims, 2 Drawing Sheets

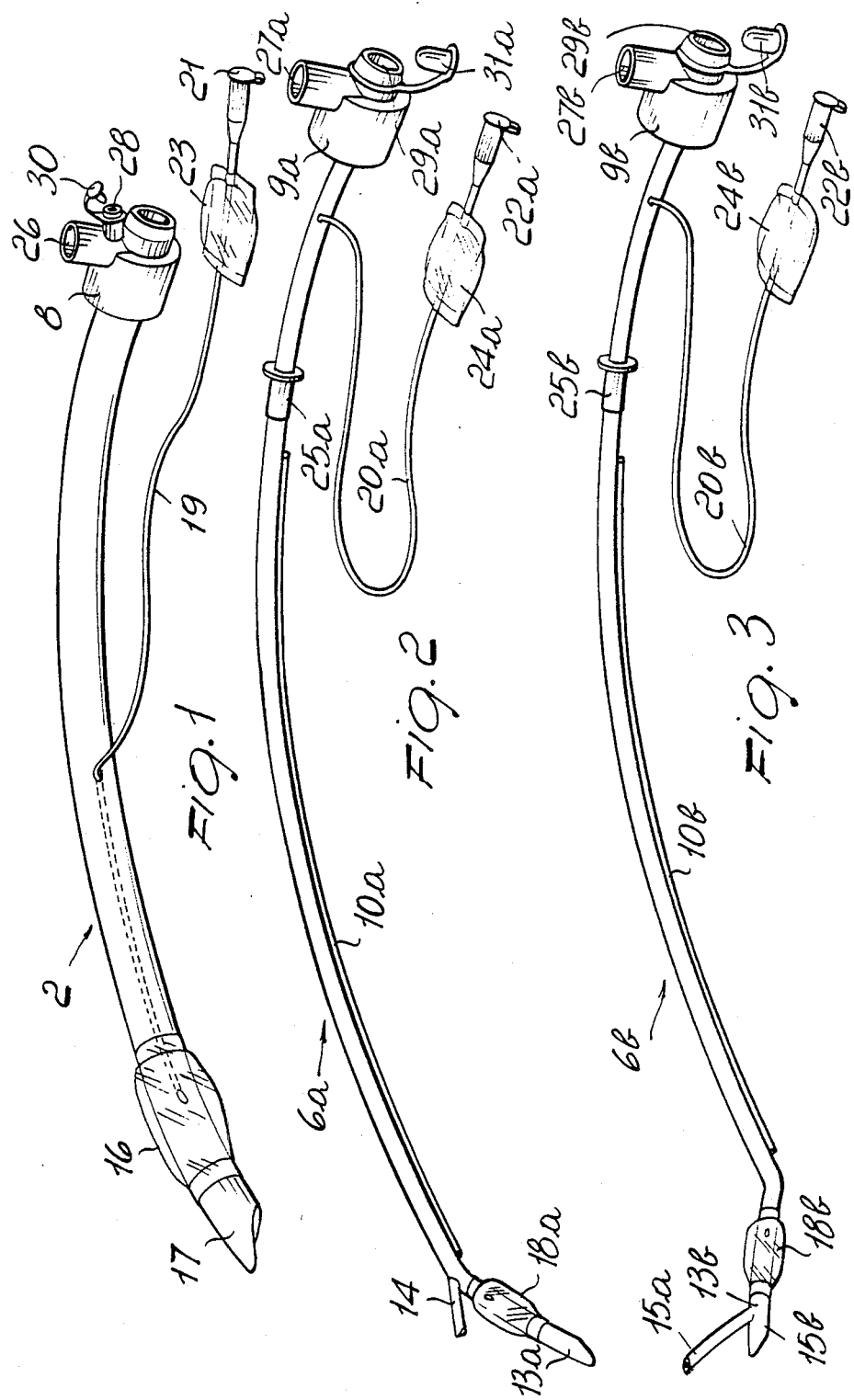

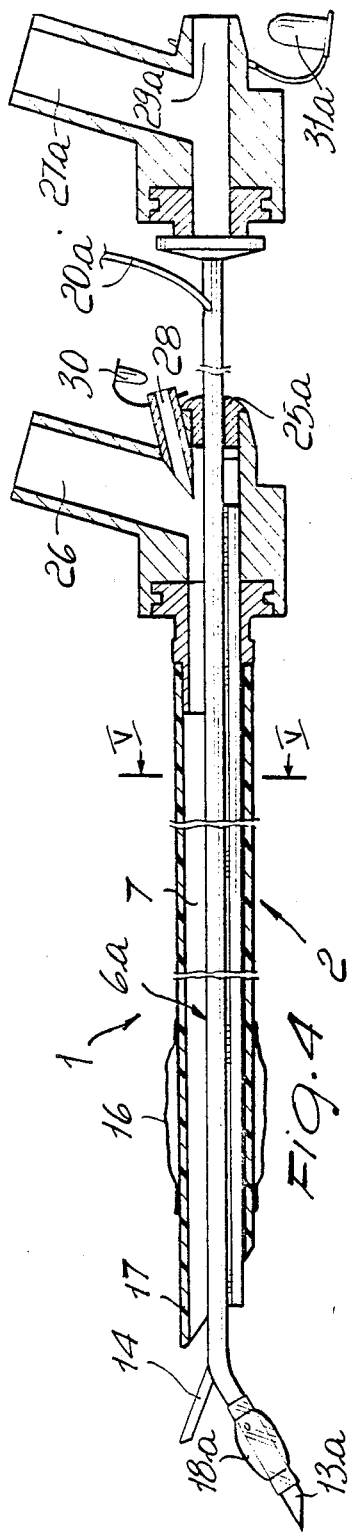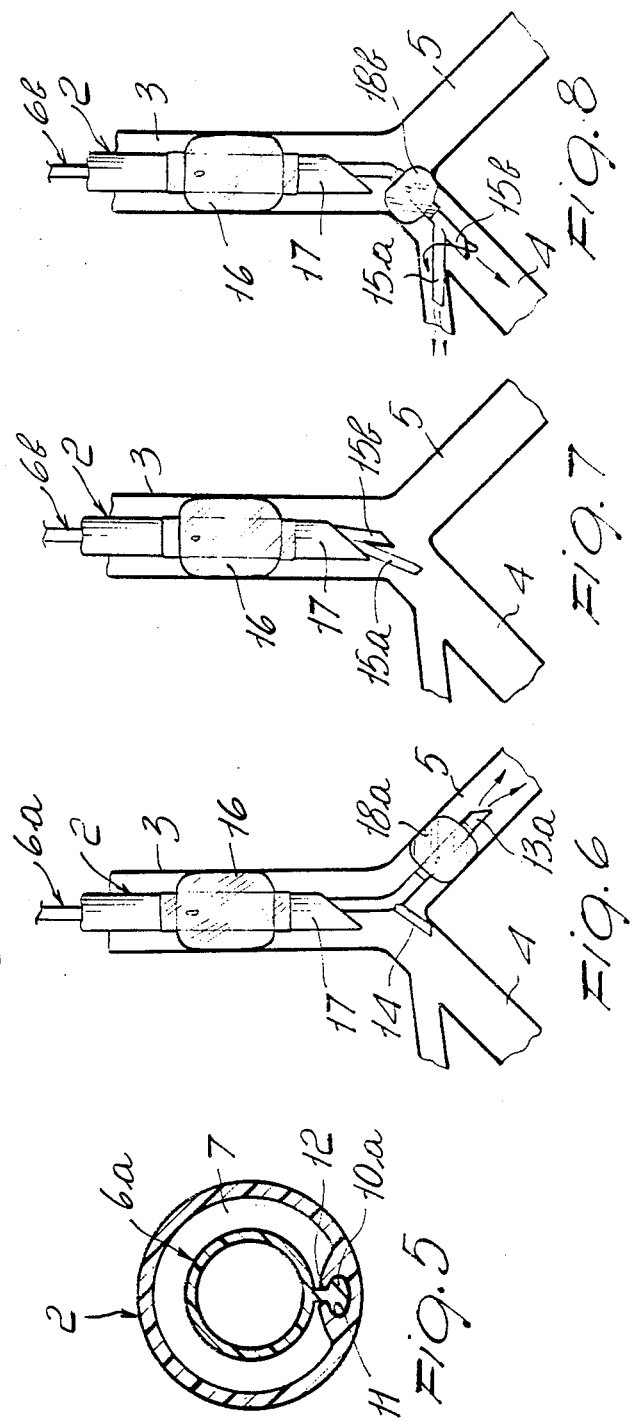

DEVICE FOR SELECTIVE BRONCHIAL INTUBATION AND SEPARATE LUNG VENTILATION, PARTICULARLY DURING ANESTHESIA, INTENSIVE THERAPY AND REANIMATION

BACKGROUND OF THE INVENTION

This is a continuation of application Ser. No. 06/890.199 filed July 8, 1986 now abandoned.

The present invention relates to an airway device for selective intubation of the bronchi and separate lung ventilation, particularly during anesthesia, intensive therapy and reanimation.

Known are devices for effecting a patient's respiration undergoing thoracic surgical interventions which generally consist of double tubes such as Carlens or White's tubes which permit separate ventilation of the two lungs. The separate ventilation of the two bronchi has several different objects, the most important of which are the following:

(1) to prevent flooding of the lateral bronchus by material squeezed from the other of the two bronchi which is the site of the surgical intervention when positioning the patient;
(2) to permit "open bronchus" surgical manoeuvres;
(3) to facilitate collapsing of the lung and surgical manoeuvres in the operating field.

These double tubes generally comprise two conduits of different lengths laid side by side, which are inserted contemporaneously into the trachea of a patient. The longest conduit terminates in one of the principal bronchi and its external walls include a hook for engagement with junction zone of the two principal bronchi to stop the tube in the correct position.

Although, in clinical practice, widespread use is made of Carlens or White's double tubes, their use is not devoid of inconveniences.

Introduction, in fact, is not always facilitated due to the greater diameter with respect to the diameter of the standard tracheal tube and due to the different form and curvature of the distal extremity which may obstruct the passage across the larynx and progression in the trachea.

Further, the correct positioning of the tube can only be controlled by auscultation and as such, it is possible that an incomplete separation of the two half-systems may pass unobserved. In addition, when positioning the patient after insertion of the tube in a lateral position for thoracotomy, it is possible that the tube may become displaced. Furthermore, the presence of the hook and the curvature of the longest tube, can occasionally cause damage to the patient during its insertion.

SUMMARY OF THE INVENTION

The main aim of the present invention is that of obviating the above cited inconveniences by realizing an airway which can be easily inserted into the patient at any time during a surgical intervention and which can achieve, with safety, separate, selective ventilation of the two lungs without causing damage to the patient.

Within the above aim an object of the invention is that of rendering the fluid-dynamic resistances at the interiors of the tracheal tube and the endobronchial tube as uniform as possible with respect to each other.

This aim and this and other objects which will become apparent hereinafter are achieved by a device for selective bronchial intubation and separate lung fluid media ventilation, particularly during anesthesia, intensive therapy and reanimation, characterized in that it comprises a tracheal tube, insertable into the trachea of a patient, at least one endobronchial tube, insertable into said tracheal tube for reaching with one of its extremities one of the principal bronchi and defining in co-operation with the tracheal tube an air passage, said tubes, at their external extremity being connectable to an air supply and at their internal extremity being provided with sealing members, sealingly engageable with the internal walls of the organs wherein said tubes are insertable, and sealing means adapted to act between the two tubes towards the exterior for preventing external communication with said air passage.

BRIEF DESCRIPTION OF THE DRAWINGS

Other characteristics and advantages of the invention will be apparent from the following description of a preferred, though not exclusive embodiment of an airway according to the invention, illustrated in the accompanying illustrative, not limitative drawings wherein:

FIG. 1 is a prospective view of the tracheal tube of the airway according to the invention;

FIG. 2 is a prospective view of an endobronchial tube for ventilation of the left principal bronchus;

FIG. 3 is a prospective view of an endobronchial tube for ventilation of the right principal bronchus;

FIG. 4 is a sectional view of the tracheal tube with the endobronchial tube inserted therein, as taken along the longitudinal mid axis;

FIG. 5 is a sectional view as taken along the line V—V of FIG. 4; and

FIGS. 6 to 8 are schematic views of the airway showing ventilation of the left principal bronchus, and the right principal bronchus.

DESCRIPTION OF A PREFERRED EMBODIMENT

With reference to the drawing figures, the airway according to the invention, indicated generally by the reference numeral 1, comprises an elongated tracheal tube 2 having a forward and a rearward end and insertable into the trachea 3 of a patient and at least one endobronchial tube, 6a, 6b, respectively, which can be inserted into and has a greater length than the tracheal tube for reaching, with its forwrad extremity, one of the principal bronchi 4,5. The endobronchial tube, when inserted into the tracheal tube, through a port or opening at the external end thereof, defines between its external surface and the internal surface of the tracheal tube a lumen or an air passage 7 such that, upon connecting the external or rearward end 8 of the tracheal tube, and the rearward extremity 9a, 9b of the endobronchial tube to a device for supplying air, of a well known type and not shown in the drawing figures for reasons of clarity, one has a flow of air passing through the endobronchial tube and through the air passage 7. The endobronchial tube and the tracheal tube, expediently have an internal cavity of circular cross section and their relative sizing is arranged such as to ensure uniform, equal ventilation of the two lungs, that is, the fluid-dynamic resistances, of the endobronchial tube and of the passage 7 are substantially, relatively equal; this fact guarantees, in parity with the delivery flow from the air supply, an equal flow of air in the two tubes. In fact the diameter of the inner peripheral surface of the cavity of the tracheal tube is greater than the diameter of the external surface of the endobronchial tube, to leave free a passage of lumen for the flow of fluid media therethrough.

As visible in FIG. 5 the endobronchial tube 6a (or 6b) has a peripheral zone at a distance from the inner surface of the tracheal tube 2.

The airway according to the invention advantageously comprises two endobronchial tubes of slightly different conformation, more precisely a first endobronchial tube 6a and a second endobronchial tube 6b which are selectively insertable into the tracheal tube according to whether one wishes to ventilate the left principal bronchus 5 or the right principal bronchus 4.

Furthermore, the airway may comprise guide means for rendering associable, in mutually slideable relationship the endobronchial tube and the tracheal tube, 6a,6b, respectively.

These guide means are of groove and tongue-like configuration and expediently comprise an expansion 10a,10b, respectively extending longitudinally along the external surface of the endobronchial tube for at least an intermediate portion of its length and is engageable, during the insertion of the endobroncheal tube into the tracheal tube, in a guide groove 11, correspondingly defined on the internal surface of the tracheal tube.

In practice the expansion 10a,10b, respectively may have a circular or oval section with a stem 12 which in association with the external wall of the endobronchial tube prevents incorrect threading of the expansion in the guide groove 11.

In this way the endobronchial tube is internally associable with the tracheal tube during the insertion and resultantly eliminates the possibility of rotation or accidental flexure of the endobronchial tube.

By virtue of the fact that the possibility of rotation of the endobronchial tube with respect to the tracheal tube is eliminated, one may provide in fact, a first endobronchial tube 6a which has an internal or rearward extremity or tip 13a inclined or bent with respect to the longitudinal extension of the expansion 10a, such that during the insertion of the first endobronchial tube into the tracheal tube, with the expansion 10a engaged in the guide groove 11, the extremity 13a is safely orientated towards the left principal bronchus. In the same way one may provide a second endobronchial tube 6b which has an internal or forward extremity 13b inclined with respect to the longitudinal extension of the expansion 10b, but in an opposite direction with respect to the inclination of the extremity 13a, such that during insertion of the second endobronchial tube into the tracheal tube, with the expansion 10b engaged in the guide groove 11, the extremity 13b is safely orientated towards the right principal bronchus.

Obviously, according to the necessity to intubate and ventilate the right principal bronchus or the left principal bronchus one inserts into the tracheal tube, the first endobronchial tube 6a or the second endobronchial tube 6b.

The first endobronchial tube 6a may comprise, proximately to the point whereat the inclination of the internal or forward extremity 13a commences, with respect to the rest of the endobronchial tube, a branch formation in the form of a hook 14, advantageously made of elastically flexible material and adapted to rest on the tracheal carinac, to stop progression of the tube when it has reached the correct position in the left principal bronchus.

Since the right principal bronchus has a different conformation with respect to the left principal bronchus in that it has a first bifurcation 4a,4b very close to the tracheal carinac, the extremity of the second endobronchial tube 6b may advantageously have a branch formation in the form of bifurcated conformation, such that during insertion, the two branches 15a, 15b of the extremity 13b can be inserted into the two branches 4a and 4b of the bifurcation of the right principal bronchus.

The two branches 15a and 15b of the bifurcation may either be both hollow, or one of these branches may define a full section, in that the branch of the extremity 13b engaged with the bifurcation of the right principal bronchus will anyway guarantee ventilation of both branches of the bronchus.

Obviously, the extremity 13b of the second endobronchial tube 6b must be made of a very flexible synthetic material to obtain, on bringing together the two branches 15a and 15b, easy insertion of the extremity 13b into the tracheal tube.

In practice, the bifurcation of the second endobronchial tube and the hook or branch 14 of the first endobronchial tube constitute means for stopping progression of the endobronchial tube when it has reached its correct position at the interior of the bronchus to be intubated.

The airway according to the invention also comprises internal sealing means comprising a first vesicle 16, formed circumferentially around the tracheal tube 2 proximately to its internal or forward extremity 17 and a second vesicle 18a,18b respectively formed circumferentially around the endobronchial tube 6a,6b respectively, proximately to its internal extremity. The vesicles 16,18a and 18b are inflatable from the exterior through feed conduits 19,20a and 20b which are at least partially located within the tubes to communicate internally with the vesicles. The admission of air into the vesicles causes their inflation and thus, their sealing engagement with the internal walls or surfaces of the tubular organs of the bronchotracheal tube system of which trachea 3 and right and left bronchi 4 and 5 respectively are shown in FIGS. 6-8, wherein the tubes are inserted, and in this way causing isolation of that part of the tubular organ located between the inflated vesicles. The external or rearward extremities of the feed conduits may be provided with caps 21, 22a, and 22b, for maintaining inflation of the vesicles and the feed conduits may include small bags 23,24a,24b, being elastically deformable for controlling the pressure exerted by the vesicles on the internal walls of the organs.

Obviously, the vesicle 18a of the first endobronchial tube 6a will be located downstream of the branch or hook 14, for secure engagement with the internal wall of the left principal bronchus, whilst the vesicle 18b of the second bronchial tube 6b is located upstream or behind of the bifurcated extremity to eliminate the possibility of obstructing with the vesicle 18b, the bifurcation of the right principle bronchus.

The airway according to the invention also comprises sealing means located towards the exterior comprising a stopper 25a,25b respectively, sealingly engageable with the external extremity 8 of the tracheal tube and sealingly slideable on the endobronchial tube. Thus isolating the air passage 7 from the exterior.

For completenes of description, it should be added tht the external extremity of the tracheal tube and the endobronchial tube are expediently provided with first ports 26,27a,27b for the connection to the air supply and second ports 28,29a,29b, closeable by means of plugs 30,31a,31b, for permitting the insertion of medical instruments such as probes and for the eventual removal of matter secreted by the organs wherein the tubes are inserted.

The operation of the airway according to the invention is the following.

Initially one proceeds by inserting the tracheal tube 2 into a patient's trachea 3, successively one inserts the endobronchial tube into the tracheal tube.

In the case where two endobronchial tubes are provided having guide means, according to which bronchus it is desired to intubate, one inserts into the tracheal tube, either the endobronchial tube 6a or the endobronchial tube 6b.

During the insertion into the tracheal tube, one bends the internal extremity 13a,13b of the endobronchial tube, utilizing the flexibility of the material of which it is made, to bring together the branches of the bifurcation or hook towards the longitudinal axis of the tube to pass easily through the tracheal tube. Whilst inserting the chosen endobronchial tube into the tracheal tube, one threads the expansion 10a,10b into the guide groove 11. In this way the endobronchial tube is slideably associated with the tracheal tube and, when the internal extremity 13a,13b exits the extremity 17 of the tracheal tube, the internal extremity 13a,13b opens to its original position, inclined with respect to the logitudinal extension of the expansion 10a,10b with secure positioning at the correct location in the selected principal bronchus. In the case where one desires to intubate the right principal bronchus, when the extremity 13b of the endobronchial tube 6b exits the internal extremity of the tracheal tube, as well as the return to the original inclination of the extremity 13b with respect to the expansion 10b, the two branches 15a,15b which were brought together during insertion, spread apart and engage in the bifurcation 4a,4b of the right principal bronchus 4, each being inserted into one of the branches 4a,4b of the bifurcation thereby stopping progression of said endobronchial tube structure 2. In the same way, when one wishes to intubate the left principal bronchus, when the internal extremity of the endobronchial tube 6a reaches the correct position, the hook 14 engages with the tracheal carina. If, in either case the operator or surgeon senses resistance opposing the ulterior insertion, he may adjourn the operation.

Successively, the operator may engage the stopper 25a or 25b in the external extremity of the tracheal tube by sliding it along the endobronchial tube to thus isolate the passage 7, and then proceeds to inflate the vesicles 16,18a,18b to form a seal with the internal walls of the organs and, after this, one may proceed to ventilte one or both of the principal bronchi.

In practice, the airway according to the invention fully achieves its objects by virtue of the passage of one tube inserted into the other, the intubation is facilitated, rendered quicker and can be effected at any time during the intervention, irrespective of the patient's position.

Another advantage resides in the provision of two endobronchial tubes, each associable, through the described guide means, with the tracheal tube, and not least the internal extremity, inclined according to the bronchus to be intubated, which reduces turbulence during ventilation of the tracheal tube and safe positioning of the endobronchial tube in the selected bronchus.

A further advantage, imparted by virtue of the fact that the extremity of the endobronchial tube for insertion into the right principal bronchus is bifurcated, and the presence of the hook on the endobronchial tube for insertion into the left principal bronchus, is that of obtaining in a simple manner, the correct positioning of the internal extremity of the endobronchial tube in the entubed bronchus.

A not least advantage is that of having a passage, between the tracheal tube and the endobronchial tube wherein one may easily insert medical instruments or probes.

Furthermore, regardless of problems or difficulties which may arise during intubation, it is always possible to obtain ventilation of at least one of the two half-systems by feeding air into the endobronchial tube or the tracheal tube.

The airway as described is susceptible to numerous modifications and variations, all falling within the scope of the inventive concept; furthermore all details may be substituted by technically equivalent elements.

In practicing the invention any dimensions or materials may be used, providing that they are compatible with the specific use, according to the contingent requirements and the state of the art.

I claim:

1. A device for selective bronchial intubation and separate lung fluid media ventilation, comprising:
   an elongated tracheal tube structure adapted to be inserted into a human trachea and having a forward end, a rearward end and a length sufficient to allow the forward end of said tracheal tube structure to be positioned in the trachea at a location near the carina defining bifurcation of the trachea into right and left main bronchi,
   said tracheal tube structure having an inner surface defining an internal cavity having an internal cavity diameter and extending lengthwise within said tracheal tube structure between said forward and rearward ends,
   first inflatable sealing means mounted on the outer periphery of said tracheal tube structure near the forwaard end thereof, said first inflatable sealing means being adapted upon inflation thereof to expand into substantial sealing contact with the inner surface of the trachea near the carina defining bifurcation thereof and
   an endobronchial tube structure defining a first lumen for the fluid passage therethrough and having an external diameter which is smaller than said internal cavity diameter, said endobronchial tube structure being removably inserted into said internal cavity of said tracheal tube structure for longitudinal sliding movement therein,
   said endobronchial tube structure having an external surface defining with said inner surface of said tracheal tube structure a second lumen for the flow of fluid media therethrough,
   said endobronchial tube structure having a rearward end portion and a forward end portion with a forward tip made of flexible material and upon insertion into said tracheal tube structure extending beyond said forward end of said tracheal tube structure and at the outside thereof, said forward end portion being bent at an angle with respect to the remaining portion of the endobronchial tube structure for insertion into the right main bronchus,
   a second inflatable sealing means on said forward end portion, said second inflatable sealing means being adapted upon inflation thereof to expand into substantial sealing contact with the inner surface of the right main bronchus behind the first bifurcation thereof, an arm of flexible material extending from said forward end portion between said tip and said second sealing means at an acute angle with respect to said forward tip, said forward end portion and said arm defining bifurcation means for positioning into the first bifurcation of the right bronchus to stop progression of said endobronchial structure, first and second duct means connectable with said first and second sealing means, respectively, and with a source of fluid pressure for inflation thereof and stopper means at said rearward end of said tracheal tube for cooperation with said endobronchial tube structure while still allowing fluid flow into and out of said second lumen.

2. A device according to claim 1, wherein said arm defines a third lumen therethrough in communication with said first lumen of said endobronchial tube.

3. A device according to claim 1, wherein said tracheal tube structure has
first elongated mating guide means facing said internal cavity and extending in the lengthwise direction of said tube, and wherein said endobronchial tube structure has on said external surface thereof
second elongated mating guide means adapted to be slidably engaged with said first elongated mating guide means, thereby preventing relative axial rotation between said tracheal tube structure and said endobronchial tube structure inserted therein and allowing lengthwise movement therein.

* * * * *